United States Patent [19]

Jennings et al.

[11] 4,102,915

[45] Jul. 25, 1978

[54] DIMERIZATION PROCESS

[75] Inventors: James Robert Jennings; Philip John Hogan, both of Runcorn, England

[73] Assignee: Imperial Chemical Industries Limited, London, England

[21] Appl. No.: 793,272

[22] Filed: May 3, 1977

[30] Foreign Application Priority Data

May 10, 1976 [GB] United Kingdom .............. 19108/76

[51] Int. Cl.$^2$ .................. C07C 120/00; C07C 121/30
[52] U.S. Cl. ............................................. 260/465.8 D
[58] Field of Search ................................. 260/465.8 D

[56] References Cited

U.S. PATENT DOCUMENTS 3,574,702   4/1971   Feldman et al. ............. 260/465.8 D

FOREIGN PATENT DOCUMENTS

| 1,522,836 | 3/1968 | France ......................... 260/465.8 D |
| 1,519,376 | 2/1968 | France. |
| 1,293,155 | 4/1969 | Fed. Rep. of Germany .... 260/465.8 D |
| 1,224,529 | 3/1971 | United Kingdom ......... 260/465.8 D |
| 1,177,182 | 1/1970 | United Kingdom. |
| 1,154,275 | 6/1969 | United Kingdom. |
| 1,036,519 | 7/1966 | United Kingdom. |

OTHER PUBLICATIONS

C.A., 62 (1965), 14508e, Badische.

*Primary Examiner*—Joseph Paul Brust
*Attorney, Agent, or Firm*—Cushman, Darby & Cushman

[57] ABSTRACT

Process for the dimerization of ACN to substantially linear $C_6$ dimers using organic phosphinites or phosphonites as catalyst, in the presence of a proton-donating solvent and optionally a hydrocarbon co-solvent, the ACN and solvent(s) being dry and at least one of the solvents having a boiling point higher than ACN and being capable of rapid phase separation with respect to the dimeric products. Enables the unreacted ACN to be removed by distillation and the solvent(s) and product to be readily separated. Preferably the catalyst partitions in favor of the solvent phase.

9 Claims, No Drawings

DIMERIZATION PROCESS

This invention relates to a dimerisation process and, especially, to a process for the dimerisation of acrylonitrile to linear $C_6$ dinitriles.

In our copending U.S. pat. application Ser. No. 736,498, filed Oct. 28, 1976, we describe a process for the dimerisation of acrylonitrile to predominantly straight-chain $C_6$ dimers, which comprises contacting the acrylonitrile with an organic phosphorus (III) compound having at least one hydrocarbyl and at least one alkoxy or cycloalkoxy group attached to the phosphorus atom or atoms, the acrylonitrile being dissolved in an organic solvent capable of donating protons, and the acrylonitrile and solvent being substantially dry.

By the use of this process, predominantly linear $C_6$ dimers of acrylonitrile, especially the 1,4-dicyanobutenes, may be prepared in good yield, the desired products being readily separated from the reaction mixture by fractional distillation or solvent extraction.

A modification of the above process, described in our copending British Patent Application No. 52887/75, involves the addition of a non-hydroxylic co-solvent, which is preferably a hydrocarbon, and gives rise to a reduction in the proportion of oligomeric and polymeric by-products.

Where the $C_6$ dinitriles are insoluble in alcohols and hydrocarbons, it has been found that when acrylonitrile is also present above a threshold concentration, a single-phase homogenous mixture results, so that separation of the acrylonitrile and solvent(s) from the reaction mixture leaves the dimeric products containing all the organic phosphorus compounds, and these may be difficult to separate.

We have now found that if one or both of said solvents has a boiling point higher than that of acrylonitrile, hereinafter referred to as a "high boiling" solvent, the unused acrylonitrile may be removed from the reacted mixture by distillation at atmospheric or higher or lower pressures, leaving the dimeric products plus the high boiling solvent or solvents as a two-phase mixture which may be readily separated, the organic phosphorus (III) compounds partitioning between the two phases and hence reducing their concentration in the product layer.

According to the present invention we provide a process for the dimerisation of acrylonitrile in which the acrylonitrile is contacted with an organic phosphorus (III) compound having at least one hydrocarbyl and at least one alkoxy or cycloalkoxy group attached to the phosphorus atom or atoms, the acrylonitrile being dissolved in an organic solvent capable of donating protons, optionally with a non-hydroxylic co-solvent, the acrylonitrile and solvents being substantially dry, and one or both of said solvents having a boiling point higher than that of acrylonitrile and being capable of rapid phase separation with respect to the dimeric products, the unreacted acrylonitrile being subsequently removed from the reacted mixture by distillation to leave the said high boiling solvent or solvents and dimeric products as a readily separable two-phase mixture.

The high boiling solvent(s) and phosphorus (III) compound catalyst should be chosen in combination so that the phosphorus compounds partition in favour of the solvent so that the concentration of unused catalyst and catalyst residues in the dimeric product is reduced as much as possible. This is readily determined by preparing mixtures containing the product and appropriate solvent/catalyst combinations, allowing the mixture to separate into two phases and then determining the concentration of catalyst in each phase. The solvent phase should also have a density as different as possible from that of the dimeric products to facilitate phase separation. Generally the solvent layer will have the lower density; but this is not essential.

The unused catalyst which is recovered in this way is usually in a form which is suitable for recycle to the process with little further treatment. In particular it is possible to reduce to a minimum additional manipulations which introduce water, oxygen and other impurities which are detrimental to the catalyst.

The presence of a proton-donating solvent is essential to our process, as in the absence of solvent rapid polymerisation of the acrylonitrile occurs. It is also preferable that the proton-donating solvent and any co-solvent is substantially unreactive with respect to addition to or reaction with the unsaturated linkage of the acrylonitrile or the dimeric reaction products. It is also essential that the solvent(s) must not react with the phosphorus compound catalyst or catalytic intermediates to form an inactive species at least at such a rate as to seriously impair catalysis of the dimerisation reaction.

Preferably the proton-donating solvent is a hydroxylic solvent, such as an alcohol, provided that it is substantially unreactive, as defined above. If the proton-donating solvent is the sole solvent it must be "high-boiling". Suitable high boiling proton-donating solvents include decanol, nonanol, octanol, iso-octanol, 2 ethyl hexanol, heptanol, phenyl dimethyl carbinol and isomers and mixtures thereof. There may be some reaction between ACN and the alcohol, the effect being most pronounced with primary alcohols. For this reason tertiary or secondary alcohols such as phenyldimethyl carbinol and octan-2-ol are preferred. However, the advantages of catalyst and product separation may be sufficiently great to allow the use of primary alcohols. When a high-boiling co-solvent is used, suitable proton-donating solvents also include t-butanol and iso-propanol.

The non-hydroxylic co-solvent is preferably a hydrocarbon. Suitable high-boiling co-solvents include decalin, petroleum ether (b.pt. > 110° C), tetralin and kerosene.

When the proton-donating solvent is high-boiling, the co-solvent need not be high-boiling; in this case suitable hydrocarbon co-solvents include hexane, cyclohexane, benzene and toluene. When present, the proportion of co-solvent in the reaction mixture may be varied over wide limits. In general the ratio of proton-donating solvent to co-solvent is in the range 1/40 to 40/1; but ratios at the lower end of the range are generally preferred. However, the final choice of solvent/co-solvent ratios will depend on how it is desired to run the process and the catalyst compound used. For example, ratios in the range 1/5 to 1/20 may give rise to enhanced catalyst lifetime and increased selectivity to linear dimer, when compared with an equivalent reaction where the ratio is 1/1.

Changes in the ratio of proton-donating solvent/co-solvent are generally reflected by changes in the amount of polymers formed and changes in the reaction rate. These changes in reaction parameters are often dependent upon the actual catalyst and solvent system chosen. For example, addition of hydrocarbons to a dimerisation system comprising acrylonitrile, tertiary butanol and isopropyldiphenylphosphinite results in a reduction in the production of polymers, but also in a reduction in the rate of reaction. The presence of a co-solvent also allows higher reaction temperatures to be used and, in some cases, has a stabilising effect on the phosphorus (III) compounds used as catalysts.

The ratio of linear to branched dimers is dependent on the solvent/co-solvent ratio in some instances. It is sometimes found that, as the proportion of proton-donating solvent decreases, the proportion of linear dimer increases and vice-versa.

Generally, the concentration of acrylonitrile in the solvent mixture should range from 5 to 75% by volume. The concentration of acrylonitrile is preferably kept as high as possible in order to optimise throughput. However, in order to achieve maximum catalyst separation from the dimeric products, the concentration of solvent should be kept as high as possible. Generally, concentrations in the range 10 to 50% by volume form a convenient compromise.

As mentioned in our aforementioned co-pending patent application, suitable organic phosphorous (III) compounds include those of general formulae:

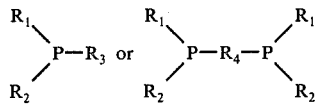

where $R_1$ is a hydrocarbyl group, $R_2$ is an alkoxy or cyclo-alkoxy group, $R_3$ is hydrocarbyl, alkoxy or cycloalkoxy group or other monovalent radical, and $R_4$ is a divalent hydrocarbyl, hydrocarbyloxy or other difunctional group. It is also possible that one or more groups $R_1$ to $R_3$ may form part of one or more ring systems.

The hydrocarbyl groups may be aryl, alkyl, alkaryl, aralkyl or cycloalkyl.

High proportions of straight-chain dimers are obtained where each hydrocarbyl group is aryl, in the case where either 1 or 2 hydrocarbyl groups are present in the phosphorus (III) compound. High reaction rates are obtained where one or both of the hydrocarbyl groups is alkyl in cases where two hydrocarbyl groups are present; but these high reaction rates may be accompanied by somewhat lower proportions of straight-chain dimers than where both hydrocarbyl groups are simple aryl. The hydrocarbyl groups may contain substituents, suitable substituent groups being halogen, cyanide, alkyl and alkoxy. High rates may also be achieved by the use of substituted aryl groups, for example, p-methoxyphenyl. The alkoxy or cycloalkoxy group or groups may contain similar substituents and may also contain aryl substituents. Examples of suitable alkoxy groups include methoxy, ethoxy, benzyloxy and isopropoxy.

Suitable examples of divalent groups $R_4$ include alkylene, polyalkylene and phenylene and polyphenylene groups, alkylene dioxy and polyalkylene dioxy groups.

Provided that the groups $R_1$ to $R_4$ do not give rise to undesirable steric effects there is no finite limit on the number of carbon atoms they may contain.

However, they will commonly contain from 1 to 10 carbon atoms.

It will be appreciated from the above that in the phosphorus (III) compounds which are useful in our invention each phosphorus atom must have at least one hydrocarbyl and one alkoxy group attached to it, but must not bear either only hydrocarbyl or only alkoxy groups. Preferred examples of phosphorus (III) compounds are phosphinites and phosphonites.

Examples of suitable phosphorus (III) compounds include diethyl phenylphosphonite, dimethyl phenylphosphonite; dimethyl p-methylphenylphosphonite, diethyl p-methylphenylphosphonite, methyl diphenylphosphinite, isopropyl diphenylphosphinite, ethyl phenylethylphosphinite, ethyl diphenylphosphinite, cyclohexyl diphenylphosphinite, diethyl p-tolylphosphonite, 2-ethylhexyl diphenylphosphinite, bis(2-ethylhexyl) phenylphosphonite, di (isopropyl) phenylphosphonite, di(neopentyl) phenylphosphonite, 2-octyl diphenylphosphinite, bis(3,5,5-trimethylhexyl) phenylphosphonite, 2-methylcyclohexyl diphenylphosphinite, 3,5,5-trimethylhexyl diphenylphosphinite, sec.butyl diphenylphosphinite, cyclohexyl diphenylphosphinite, benzyl diphenylphosphinite, $Ph_2PO(CH_2)_4OPPh_2$,

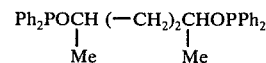

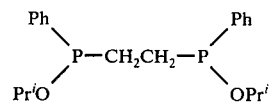

We have found that phosphinites of formula $Ph_2P(OisoPr)$ are especially useful in our process, as they partition very favourably with respect to many suitable high boiling solvents. As used herein, the term "Ph" refers to phenyl.

The concentration of the phosphorus compound in the reaction mixture may be varied over a wide range, for example, from 0.01, preferably 0.05 to 5% by volume, calculated on the volume of liquid reactants; but preferably the concentration is in the range 0.05 to 3% by volume.

The reaction temperature is commonly in the range 0° to 120° C; but it is generally preferred to keep the range temperature below 75° C to minimise polymerisation of the acrylonitrile and dimeric products. Preferably, the reaction temperature is in the range 20° to 70° C. It is noted that the reaction will proceed below 0° C, maintaining selectivity, but at a reduced rate.

An essential feature of the present invention is that the reaction must be conducted in the substantial absence of water. Without prejudice to our invention, we believe that the water reacts with the catalyst in the presence of acrylonitrile to give non-catalytic addition compounds. Thus the acrylonitrile, proton-donating solvent and cosolvent must be dried before use, otherwise the reaction may be completely inhibited. In particular acrylonitrile, which commonly contains as much as 4000 ppm of water, even after distillation, must be rigorously dried. It is also noted that hydroquinone stabilisers, which are present in acrylonitrile as supplied, should be removed. For example, if the reactants contain 300 ppm of water, reaction is seriously inhibited at a concentration of the phosphorus compound of 0.5% by volume; but at water concentrations of 50 ppm or lower reaction takes place readily. Any suitable drying technique may be used, provided that the final water level is sufficiently low. For example, acrylonitrile and hydroxylic solvents may be dried by being contacted with calcium hydride or a 3A or 4A molecular sieve. The above findings contrast strongly with the teaching of the prior art which makes no mention of removal of water and/or hydroquinone stabilisers, and in many instances advocates the addition of water and stabilisers, such as hydroquinone, to the reaction mixture. It will be appreciated that at higher concentration of water, e.g. 300 ppm, it may be possible to cause the reaction to proceed by adding much larger amounts of catalyst. If this is done, selectivity is generally unaffected; but the process would become commercially unattractive because of high catalyst usage.

The dimeric products of our invention are predominantly linear $C_6$ dinitriles, especially the 1,4-dicyanobutenes. Selectivities >90% may be readily obtained and selectivities as high as 98% have been obtained using our most advantageous catalysts.

When conversion of ACN to dimeric products has reached the desired level, the unreacted acrylonitrile and any volatile solvent which may be present is removed by fractional distillation, leaving the dimeric products plus the high boiling solvent or solvents. The mixture is allowed to separate into two phases and the upper, or solvent, phase is separated, together with an appropriate proportion of the phosphorus (III) compounds. The reaction may be performed batchwise or continuously.

It will be appreciated that by using the above process, the separations achieved allow recycle of unreacted acrylonitrile and catalyst solution, requiring only make-up of the components consumed.

The invention will be illustrated by the following Examples, in which all parts are by weight.

In all the Examples, except where otherwise stated, the acrylonitrile was dried before use by means of calcium hydride. This was accomplished by adding powdered calcium hydride to the acrylonitrile overnight, then decanting the acrylonitrile on to fresh calcium hydride power and refluxing for 30 minutes. The acrylonitrile was then distilled from the calcium hydride. Water levels were found to be in the range 30–80 ppm after this procedure. The acrylonitrile was dried finally by storing over freshly activated 3A molecular sieve to give levels below 15 ppm.

The phosphorus (III) compounds used in the Examples are either commercially available or were prepared using methods given in "Organo-Phosphorus Compounds", Kosalapoff and Maier published by Wiley 1972, Vol. 4, Chapters 10 and 11.

An analyses of dimeric products were made by gas chromatography.

In all the Examples, "% conversion" indicates the % by weight of acrylonitrile (ACN) converted to total dimeric, oligomeric and polymeric products; the "% yield" of a product is the weight of that product calculated as a % of the weight of ACN converted; and the "Selectivity" or "% linear" as the proportion of straight-chain linear dimers, calculated on the total dimeric product.

EXAMPLE 1

Acrylonitrile (39.34 parts), nonyl alcohol (41.81 parts) decalin (43.65 parts) and isopropyl diphenylphosphinite (1.1121 parts) were placed in a RB flask fitted with a reflux condenser and maintained at 74° C for 5 hours under nitrogen. At the end of this time, solids (presumably hexamer) which were precipitated during the reaction were filtered off under nitrogen and unreacted acrylonitrile in the filtrate was removed by vacuum distillation. The filtrate spontaneously formed into two immiscible phases and the lower, dimer containing phase was separated. The upper solvent phase contained most of the catalyst, and this solution was returned to the reactor together with fresh acrylonitrile and the procedure repeated. The hexamer was washed with acetone, and the washings were added to the lower phase which was then analysed by glc for dicyanobutene-1 (DCB-1) and α-methyleneglutaronitrile (MGN). The results are shown in tabular form below:

| Cycle | Wt DCB-1 | Wt MGN |
|---|---|---|
| 1 | 8.26 | 0.42 |
| 2* | 10.50 | 0.53 |
| 3 | 4.08 | 0.20 |
| 4 | 3.89 | 0.24 |
| 5* | 10.37 | 0.78 |
| 6 | 3.68 | 0.25 |
| 7 | 2.43 | 0.16 |
| Total | 43.21 | 2.68 |

*left for 24 hours at 20° C

EXAMPLE 2

Acrylonitrile (39.75 parts), nonyl alcohol (39.15 parts), toluene (43.70 parts) and isopropy-diphenylphosphinite (1.1314 parts) were placed in a RB flask fitted with a reflux condenser and maintained at 74° C for 5 hours under nitrogen. At the end of this time, solids (presumably hexamer) which were precipitated during the reaction were filtered off under nitrogen and unreacted acrylonitrile together with some toluene in the filtrate were removed by vacuum distillation. The filtrate spontaneously formed into two immiscible phases and the lower, dimer containing phase was separated. The upper solvent phase contained most of the catalyst, and this solution was returned to the RB flask. The solution was made up to approximately the initial composition by addition of toluene and acrylonitrile. The procedure was repeated. The hexamer was washed with acetone. The washings and lower phase were analysed as described in the previous example. The results are shown below:

| Cycle | Wt DCB | Wt MGN |
|---|---|---|
| 1 | 6.09 | 0.31 |
| 2* | 11.63 | 0.60 |
| 3 | 9.67 | 0.55 |
| Total | 27.39 | 1.46 |

*left for 24 hours at 35° C.

What we claim is:

1. In a process for the dimerisation of acrylonitrile to predominantly 1,4-dicyanabutene straight-chain $C_6$ dimers, in which an organic phosphorus compound of the formula:

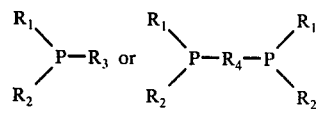

where $R_1$ is a hydrocarbyl group, $R_2$ is an alkoxy or cycloalkoxy group, $R_3$ is a hydrocarbyl, alkoxy or cycloalkoxy group and $R_4$ is a divalent hydrocarbyl or hydrocarbyloxy group, is brought into contact with acrylonitrile dissolved in an organic solvent capable of donating protons and substantially unreactive with respect to acrylonitrile and the dimeric reaction products, optionally with a non-hydroxylic co-solvent, at a temperature from 0° to 120° C, the concentrations of acrylonitrile and phosphorus compound being in the range 5 to 75% and 0.01 to 5% by volume, respectively, the acrylonitrile and solvent or solvents being substantially dry and free from acrylonitrile stabilizers, the improvement which comprises selecting one or both of said solvents to have a boiling point higher than that of acrylonitrile and being capable of rapid phase separation with respect to the dimeric products, to enable the unreacted acrylonitrile to be removed from the reacted mixture by distillation to leave the said high boiling solvent or solvents and dimeric products as a readily separable two-phase mixture.

2. A process as claimed in claim 1 in which the high boiling solvent or solvents and phosphorus compound are chosen in combination so that the phosphorus compound partitions in favour of the solvent or solvents.

3. A process as claimed in claim 1 in which the solvent phase is chosen so as to have a density which is as different as possible from that of the dimeric products.

4. A process as claimed in claim 1 in which the proton-donating solvent is a hydroxylic solvent.

5. A process as claimed in claim 4 in which the hydroxylic solvent is the sole solvent.

6. A process as claimed in claim 4 in which the hydroxylic solvent is decanol, nonanol, octanol, isooctanol, 2-ethylhexanol, heptanol or phenyldimethyl carbinol.

7. A process as claimed in claim 1 in which the non-hydroxylic co-solvent is a hydrocarbon.

8. A process as claimed in claim 7 in which the co-solvent is decalin, a petroleum ether having a boiling point >110° C, tetralin or kerosene.

9. A process as claimed in claim 7 in which the proton-donating solvent is high boiling and the hydrocarbon co-solvent is hexane, cyclohexane, benzene or toluene.

* * * * *